(12) United States Patent
Shah et al.

(10) Patent No.: US 11,357,975 B2
(45) Date of Patent: Jun. 14, 2022

(54) CYLINDRICAL MICROELECTRODE ARRAY FOR NEURAL STIMULATION AND RECORDING

(71) Applicant: Lawrence Livermore National Security, LLC, Livermore, CA (US)

(72) Inventors: Kedar G. Shah, San Francisco, CA (US); Supin Chen, Palos Verdes, CA (US); Sarah H. Felix, Oakland, CA (US); Satinderpall S. Pannu, Pleasanton, CA (US); Susant Patra, Brentwood, CA (US); Vanessa Tolosa, Oakland, CA (US); Angela C. Tooker, Dublin, CO (US); Jason Jones, Berkeley, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/580,640

(22) PCT Filed: Jun. 9, 2016

(86) PCT No.: PCT/US2016/036775
§ 371 (c)(1),
(2) Date: Dec. 7, 2017

(87) PCT Pub. No.: WO2016/201151
PCT Pub. Date: Dec. 15, 2016

(65) Prior Publication Data
US 2018/0169406 A1    Jun. 21, 2018

Related U.S. Application Data

(60) Provisional application No. 62/173,271, filed on Jun. 9, 2015.

(51) Int. Cl.
*A61N 1/05* (2006.01)
*A61N 1/04* (2006.01)
*A61B 5/24* (2021.01)

(52) U.S. Cl.
CPC .............. *A61N 1/0551* (2013.01); *A61B 5/24* (2021.01); *A61N 1/04* (2013.01); *A61N 1/0529* (2013.01);
(Continued)

(58) Field of Classification Search
None
See application file for complete search history.

(56) References Cited

U.S. PATENT DOCUMENTS

| 2009/0132042 A1* | 5/2009 | Hetke | ................ A61B 5/04001 |
| | | | 623/11.11 |
| 2011/0112591 A1* | 5/2011 | Seymour | .............. A61B 5/0084 |
| | | | 607/3 |

(Continued)

*Primary Examiner* — Ankit D Tejani
(74) *Attorney, Agent, or Firm* — James S. Tak

(57) ABSTRACT

A cylindrical microelectrode array having an elongated cylindrical core, and a multilayer structure conformally folded around and affixed to the cylindrical core so as to extend between opposite ends of the core. The multilayer structure has integrated sections including an electrode section with electrodes exposed through electrically insulating layers, a connector section with conductive bond pads for interfacing with external electronics, and a cable section with conductive traces encapsulated in electrically insulating layers and which connect between the electrodes and their corresponding bond pads. The array may be fabricated using a planar multilayer structure having the electrode, connector, and cable sections, and conformally folding the multilayer structure around and affixing to the cylindrical core. The cable section in particular may be conformally (Continued)

coiled around and affixed to the cylindrical core so that the electrical conduits helically extend between the connector and electrode sections.

9 Claims, 9 Drawing Sheets

(52) U.S. Cl.
CPC ... *A61B 2562/046* (2013.01); *A61B 2562/125* (2013.01)

(56) References Cited

U.S. PATENT DOCUMENTS

| | | | | |
|---|---|---|---|---|
| 2013/0090525 | A1* | 4/2013 | Seymour | A61N 1/0534 600/104 |
| 2014/0303703 | A1* | 10/2014 | Mercanzini et al. | A61N 1/37205 607/116 |
| 2015/0080882 | A1* | 3/2015 | Skinner | A61M 25/1002 606/41 |
| 2015/0133761 | A1* | 5/2015 | Vetter | H01R 43/26 600/378 |

* cited by examiner

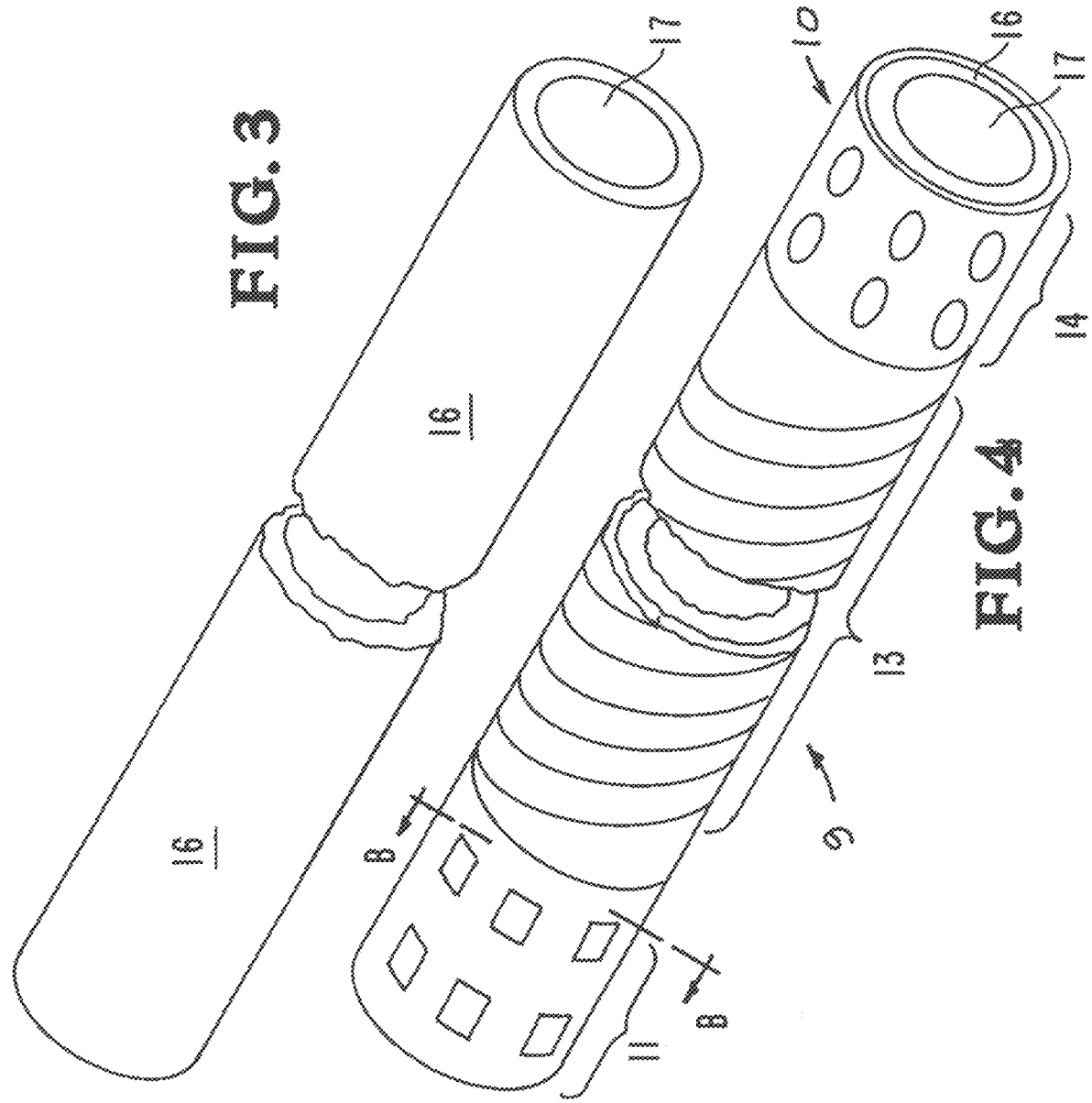

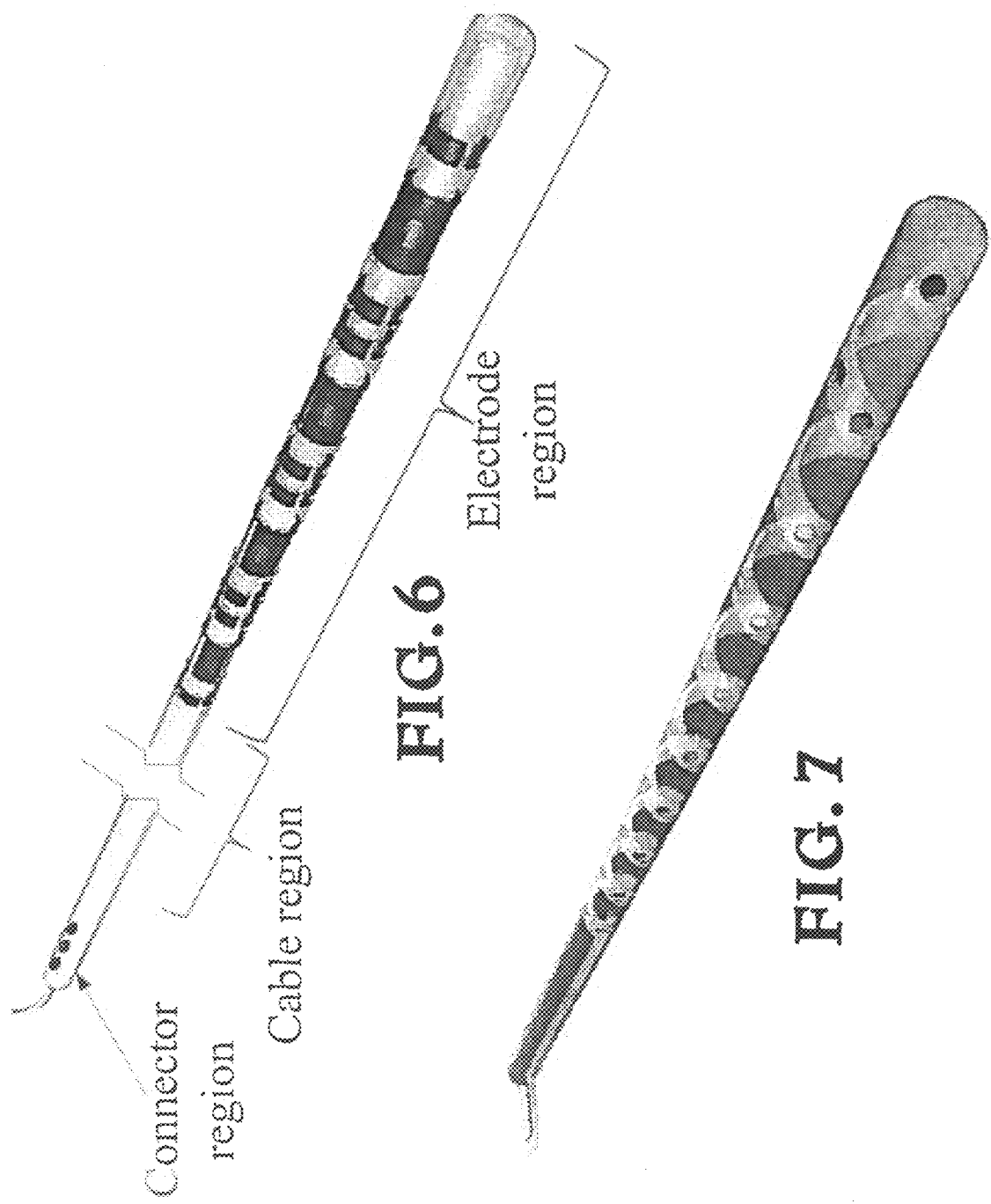

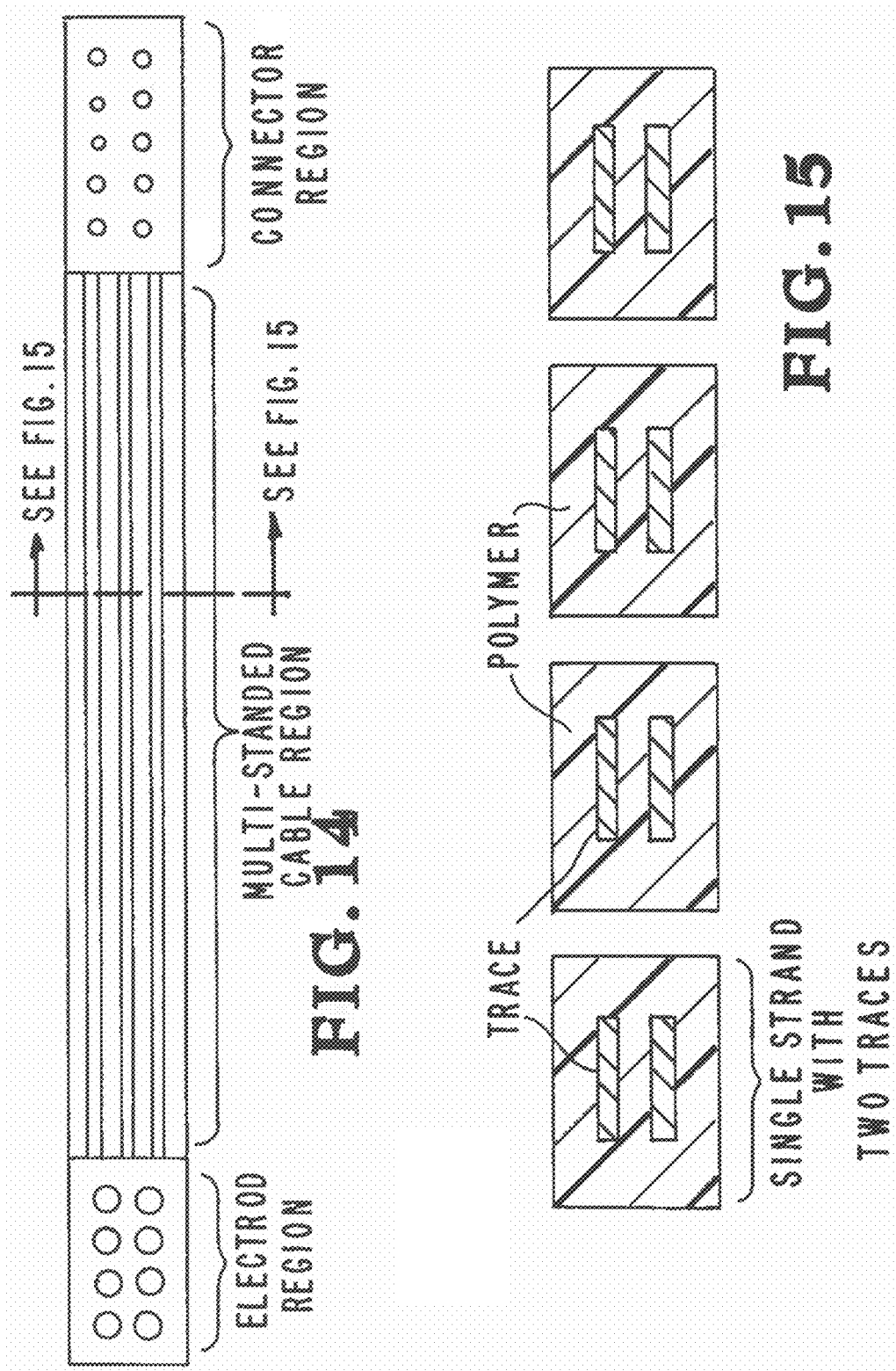

CYLINDRICAL MICROELECTRODE ARRAY FOR NEURAL STIMULATION AND RECORDING

CROSS-REFERENCE TO RELATED APPLICATIONS

This application claims the benefit of U.S. provisional application No. 62/173,271 filed Jun. 9, 2015, which is incorporated by reference herein.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Various methods are known for interfacing electrode arrays and implanted electronics with regions in or on the surface of neural tissue. And two main types of neural interface devices are known, including neurostimulators, and closed-loop neuromodulation systems. Most neurostimulators are open-loop systems that direct electrical stimulation (voltage or current pulses) into regions of the tissue where an electrode array has been implanted. The clinician can adjust the parameters of stimulation such as amplitude, frequency, bipolar vs. monopolar stimulation, and selection of which contacts to stimulate on. Recent advances in the field have led to closed-loop neuromodulation systems that detect biomarkers or signatures from recorded neural activity. These biomarkers are used to trigger neural stimulation in the same or different region of the brain. Some of the limitations with current devices are, for example: limited number of electrodes; large size, high battery consumption; inability to target multiple anatomical targets due to the size of the implants; and inability to record from small populations of neurons. However, even with the limitations of these devices, many clinical trials have been performed with varying degrees of success such as Parkinson's, essential tremor, epilepsy, turrets, obsessive-compulsive disorder, major depression, and dystonia.

Current neural interface technology uses fabrication methods that were previously developed for pacemakers. The electrode arrays that interface with the tissue are typically hand-made using platinum discs welded to insulated platinum wire. Many such discs (typically 4-8) are molded together into a cylindrical construct, where each metal disc acts as an individual electrode, or an interface with the tissue. This technology significant limits the miniaturization and density of contacts. First, the metal discs need to be large enough for welding platinum wire. Second, the electrodes form a band around the cylinder, so there is no ability to control electrical stimulation or recording around the cylinder.

As the need for accurate control of stimulation in multiple regions of the brain grows, there is a greater need for reliable microelectrode arrays having a high density of electrodes, and a method of fabricating such microelectrode arrays.

SUMMARY

One aspect of the present invention includes a cylindrical microelectrode array, comprising: an elongated cylindrical core; and a multilayer structure conformally folded around and affixed to the cylindrical core so as to extend between opposite ends thereof, said multilayer structure having integrated sections comprising: an electrode section having a plurality of electrodes exposed through electrically insulating layers, a connector section having a plurality of conductive bond pads exposed through electrically insulating layers for interfacing with external electronics, and a cable section connecting between the electrode and connector sections, and having a plurality of conductive traces encapsulated in electrically insulating layers and which connect between the electrodes and their corresponding bond pads.

Another aspect of the present invention includes a method of fabricating a cylindrical microelectrode array, comprising: providing a planar multilayer structure having an electrode section with a plurality of electrodes exposed through electrically insulating layers, a connector section having conductive bond pads for interfacing with external electronics; and a cable section having insulated electrical conduits connecting between the bond pads of the connector section with the electrodes of the cylindrical electrode section; and conformally folding the planar multilayer structure around and affixing to a cylindrical core so that the plurality of electrodes are distributed radially and/or axially along a cylindrical axis of the cylinder core.

The present invention is generally directed to a microfabricated cylindrical electrode array for neural recording and stimulation, and a method of fabricating and assembling such a cylindrical microelectrode array. The main components of this device are an elongated cylindrical core (e.g. polymeric core), and a planar multilayer structure which includes the electrodes, conductive traces, contact pads, and the insulating layers surrounding them. The planar multilayer structure is conformally folded around and affixed to the cylindrical core to form an assembly that is the cylindrical electrode array. In particular, the planar multilayer structure includes (1) an electrode section or region consisting of exposed electrodes or contacts when folded into a a cylindrical structure around the cylindrical core, (2) a connector section or region consisting of electrical bond pads to make electrical connection to an electronics module, and (3) a cable section or region consisting of individually insulated wires that are coiled around the cylindrical core as it extends between the electrode and connector regions. The cylindrical electrode array may also be configured with a hollow center so that a stylet (i.e. a mechanically rigid structure) may be used by sliding in the hollow center to insert and implant the device into tissue.

Fabricated in this manner, the fabricated cylindrical electrode array of the present invention can also be characterized as having a cylindrical electrode section or region, a connector section or region, and a cable section or region, as shown schematically in FIG. 6. The cylindrical electrode region includes a high-density of electrodes for stimulation of and/or recording from neural tissue. The electrodes can be of varying sizes and shapes, and are distributed radially and/or axially along the cylindrical structure. The electrode region forms the distal end of the cylindrical electrode array. The connector region includes conductive bond pads that are designed to interface with electronics capable of neural stimulation and recording. The electronics (not shown) are housed in a hermetic package, with a connector mechanically connecting the connector region to the package, while providing isolated electrical conduits between both components. The connector region forms the proximal end of the cylindrical electrode array. And the cable region electrically and mechanically connects the electrode region to the connector region. This cable region of the multilayer structure may consist of stiff materials (polymers, metals, and/or ceramics) that are formed into a mechanically flexible structure. In one embodiment of this device, the cable region and the electrode region of the electrode array may be combined into a single structure, such as the single, coiled structure shown in FIG. 7, where both the electrode and cable sections are helically coiled conformally around a cylindrical core. All three regions of the device may have the same diameter, or the three electrode array regions have varying diameters. In one embodiment of this device, the cylindrical electrode array may contain a hollow center lumen or gap. This allows for a long, mechanically rigid component, e.g. a stylet, to be placed through the center lumen for handling and surgical guidance of the electrode array. In another embodiment of this device the distal end of the electrode array may be sealed with a polymer cap.

Generally, the cylindrical electrode array of the present invention is microfabricated, and the multilayer structure comprises alternating layers of insulators and conductors. Both of these materials are patterned lithographically so that individual conductive traces can form electrical connections from the electrodes to connector pads. The electrodes may be fabricated of a conductive material (metals such as Pt, Ir, Au, Ta, Ru, Ti, and alloys there-of, and biocompatible stainless steel alloys). The insulator may consist of, for example, a polymer material such as but not limited to parylene, polyimide, polyurethane, and liquid crystal polymer. The top layer of insulator is etched so as to expose the electrode material and also the connector pads. Multiple layers of metal may be used to increase density of the metal traces along the cable region. Also, multiple layers allow the traces to be routed underneath the top metal layer electrode in order to increase electrode size and density. The electrode array may contain a reference electrode for differential neural recording across two electrodes. The electrode array may also contain a counter electrode that acts as a return path for the stimulation current exiting a stimulation electrode.

The electrical properties of the cylindrical electrode array of the present invention may be configured in order to enable simultaneous recording and stimulation from multiple electrodes. This may serve to ensure that a channel recording a signal is not saturated with artifact from a stimulating channel nearby. Inter-trace capacitance is minimized by using multiple layers of metal separated by insulating polymer, by increasing the gap between traces on the same metal layer, and/or by placing electrodes in a staggered or offset manner across layers to maximize distance between them. Electrical resistance is minimized by using a thick film of metal as the trace layer. FIG. 8 shows a cross-section of an example polymer electrode array showing staggered overlapping trace arrangements designed to reduce crosstalk between stimulation and recording channels.

In the present invention, the longevity of a microelectrode array may also be increased by separating the trace layer from the electrode layer on different metal layers using a vertical interconnect (or via) that is formed in the insulating polymer layer that is between both metal layers. An example of this system is shown in FIG. 9, illustrating a cross-section of an example embodiment of the cylindrical electrode array showing vertical interconnects separating the electrode layer from the trace layer, while maintaining electrical connection. This is different from prior methods where electrodes are placed on the same metal layer as the electrical traces that run from the connector to the electrode regions. In such cases, if moisture penetrates the electrode opening, it can cause shorts to form between adjacent traces on the electrode layer.

In the present invention, mechanical robustness of the electrodes and connector/bond pads may also be increased by configuring the electrode shapes and designs so as to reduce the stress on the electrode array, and prevent cracking and/or deformation of the electrode array. FIGS. 10A-C below summarizes the difference between the electrodes, depicted as top views and simplified cross-sectional views. FIGS. 10B and 10C show optional features of the present invention. FIG. 10A shows a standard electrode in which a base polymer is deposited, an electrode metal is deposited and patterned, a top layer of polymer is deposited, and an opening in the polymer is opened to create the electrode site. In this scenario, if the electrode opening is sufficiently large, the structure can buckle or bend to release stress. Another cause for buckling is the asymmetric structure where there is no polymer above the electrode to balance the stress profile. In FIG. 10B, a segmented electrode is presented in which a series of small electrode pads form a single large electrode. The small electrode pads are all interconnected with traces, and the gaps between them are covered with the top polymer layer. This segmented electrode reduces the total stress of the electrode structure and reduces buckling or curling. Additionally, the top polymer segments help balance the asymmetry present in the standard electrode. In FIG. 10C, the metal electrode is continuous, but the insulating polymer is kept intact over many regions of the electrode, thereby acting as a mechanical member that balances stress of the electrode array. The top polymer may be etched as a checkerboard pattern.

The example embodiments of FIGS. 10B and 10C are different from prior methods in traditional neural interfaces, where the electrode comprises a hulk material that can be plastically deformed into a cylindrical shape and then incorporated into the cylindrical cross-section of the electrode array. In most microfabricated devices, the size of the electrode is dictated by the lithography mask dimensions, which enables scalability from small to large contacts. The thickness of the electrode material is typically limited due to the nature of physical or chemical vapor deposition. The resulting films cannot easily be plastically deformed into cylindrical contacts since in addition to their thin-ness, they are deposited on polymers that are thicker and dominate the mechanical stiffness. For microfabricated electrodes, great care needs to be taken to reduce the stress of the metal conductor as deposited, else the structure can crack or deform in an uncontrolled manner to release the stress. This stress typically increases with greater metal deposition thicknesses.

Possible uses of the present invention include, for example: treatment of neuropsychiatric disorders (such as addiction, post-traumatic stress disorder, traumatic brain injury, borderline personality disorder, major depression, chronic pain), movement disorders (such as Parkinson's, dystonia), epilepsy, obsessive compulsive disorder, etc. For use in treatments including electrical recording or stimulation of tissue (central or peripheral nervous system)

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 3 is a perspective view of an elongated cylindrical core of the first example embodiment of the present invention.

FIG. 4 is a perspective view of the assembled first example embodiment of the cylindrical electrode array of the present invention, showing the multilayer structure conformally folded around and affixed to the cylindrical core.

FIG. 6 is a perspective view of an example embodiment of the cylindrical electrode array of the present invention.

FIG. 7 is a perspective view of a second example embodiment of the cylindrical electrode array of the present invention, wherein the electrode and cable sections form a continuous helical coil around the cylindrical core.

FIG. 14 is a top view of a second example embodiment of the present invention where the cable section comprises a plurality of strands in a multi-stranded cable configuration.

FIG. 15 is a cross-sectional view of the cable section of FIG. 14 showing each strand having two traces.

DETAILED DESCRIPTION

Figure 1:
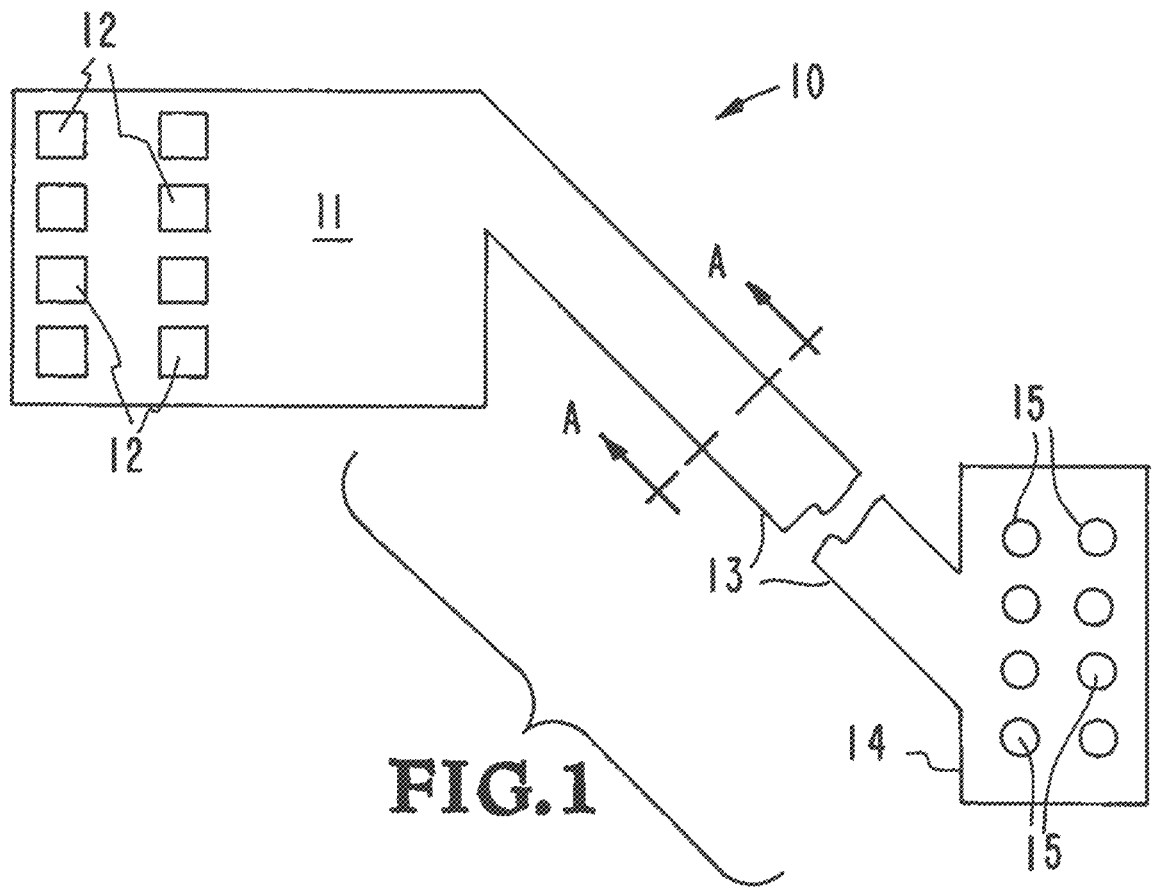
FIG. 1 is a top view of a planar multilayer structure of a first example embodiment of the present invention.
Figure 2:
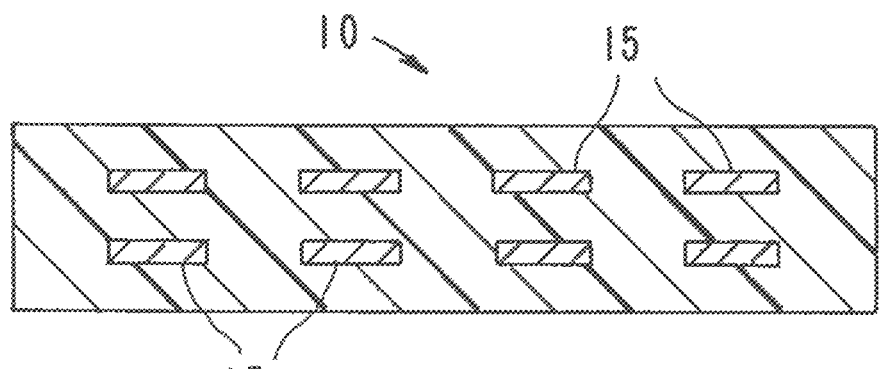
FIG. 2 is a cross-sectional view taken along line A-A of FIG. 1.
Figure 5:
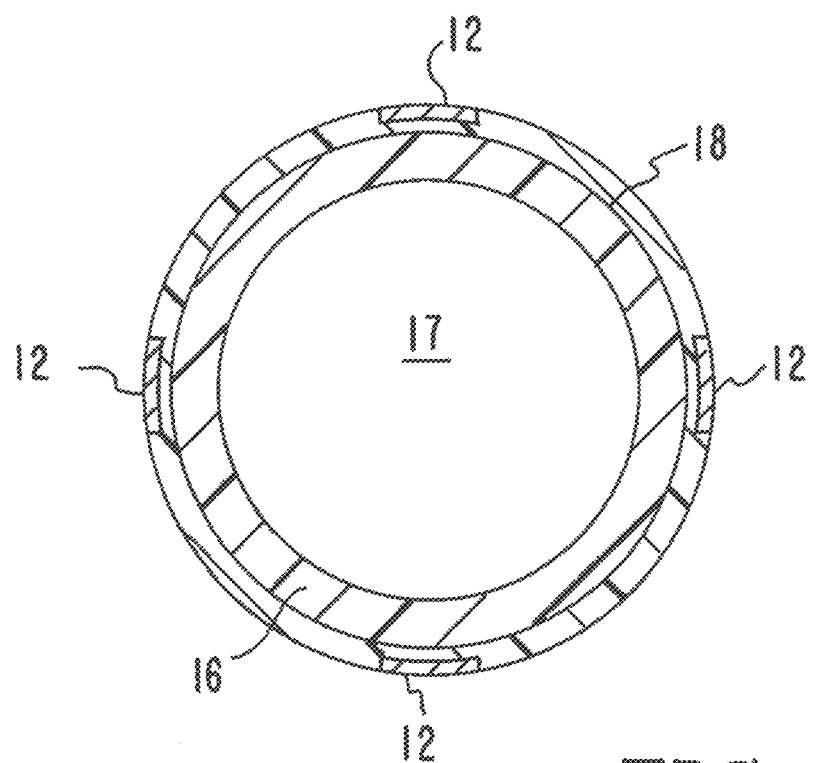
FIG. 5 is a cross-sectional view taken along line B-B of FIG. 4.
Figure 8:
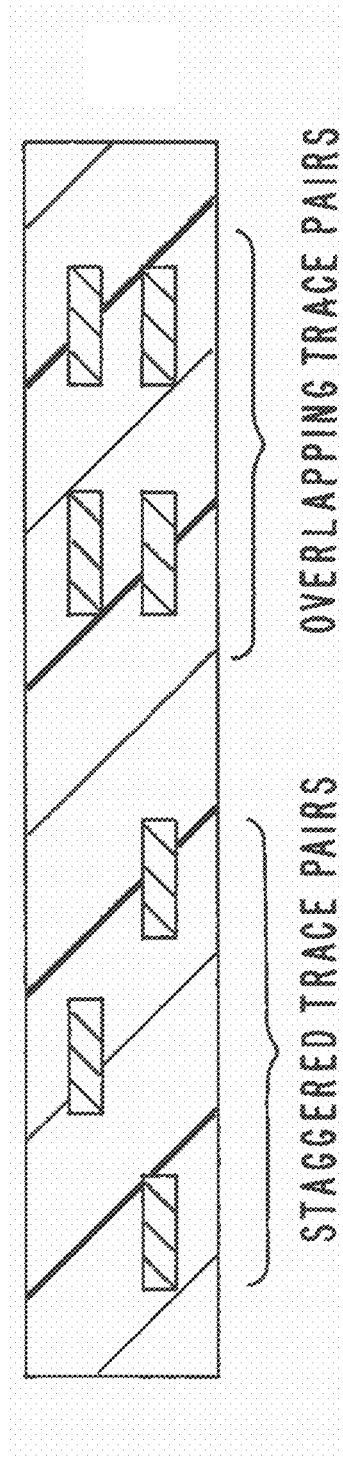
FIG. 8 is a cross-sectional view of an example polymer electrode array showing staggered overlapping trace arrangements designed to reduce crosstalk between stimulation and recording channels

FIGS. 4 and 5 shows a first example embodiment of the cylindrical electrode array of the present invention, generally shown at reference character 9, and FIGS. 2-3 show various components of the first example embodiment of the cylindrical electrode array 9. In particular, FIG. 1 shows an example flexible planar multilayer structure 10, FIG. 3 shows a cylindrical core 16 having a hollow center 17, and FIG. 4 shows the flexible planar multilayer structure 10 after being conformably affixed to the cylindrical core 16 so as to form the long, slender cylindrical assembly 9 that is the cylindrical electrode array. The multilayer structure 10 (and the assembly 9) has a cylindrical electrode section 11 at one end (for neurostimulation) having a plurality of electrodes 12. The electrode region 11 is shown having a rectangular shape where the width of the rectangle is approximately equal to the circumference of the cylindrical core 16. The length of the electrode region is approximately equal to the span of the electrodes across the electrode region. A connector region 14 is also shown having connector/bond pads where the electrode array is bonded to an electronics module. A packaged electronics assembly (not shown) may be attached at on the opposite end of the cable section. And finally the cable section 13 is shown connected between the connector section 14 and the electrode section 11. FIG. 2 shows a cross section taken along line A-A in FIG. 1, showing eight representative traces 15. In this embodiment, the electrode section and the cable section are shown having approximately the same outer diameter. And FIG. 4 shows the multilayer structure 10 conformally folded around the cylindrical core 16. As shown in FIG. 5, a seam 18 is formed along opposite edges of the electrode region. The seam may be formed by various methods, such as for example interdigitated fingers.

As described in the Summary, the planar multilayer structure consists of alternating layers of an insulating polymer (for example, polyimide) and patterned metal (for example, a platinum alloy) traces and electrodes. The insulating layer has openings that expose areas of the pattered metal layer(s) to expose electrodes and bond pads and to form vias between metal layers. A single planar structure is patterned to construct all sections of the multilayer structure. The flat pattern (e.g. planar layout) used to construct the electrode section is generally rectangular in shape, where the length of the flat pattern is approximately the same as the length of the electrode section, and the width of the flat pattern is approximately equal to the outer circumference of the electrode section.

The planar structure that forms the electrode section may include features along the long edge of the rectangle to help align the edges of the cylinder and/or to prevent delamination of the rectangular flat patter from the core. Examples of features that can be used to perform these functions include interdigitated fingers, perforations, or other such structures. Perforations may also be placed along the end of the rectangular section to as to promote adhesion of the core material and outer jacket at the tip of the final device.

The cable section of the device consists of a polymer core around which a planar structure is wound into a helix. This helix may be formed by any number of techniques, but in this embodiment it is formed by coiling the planar structure around a flexible cylindrical rod which acts as the core material.

Figure 11:
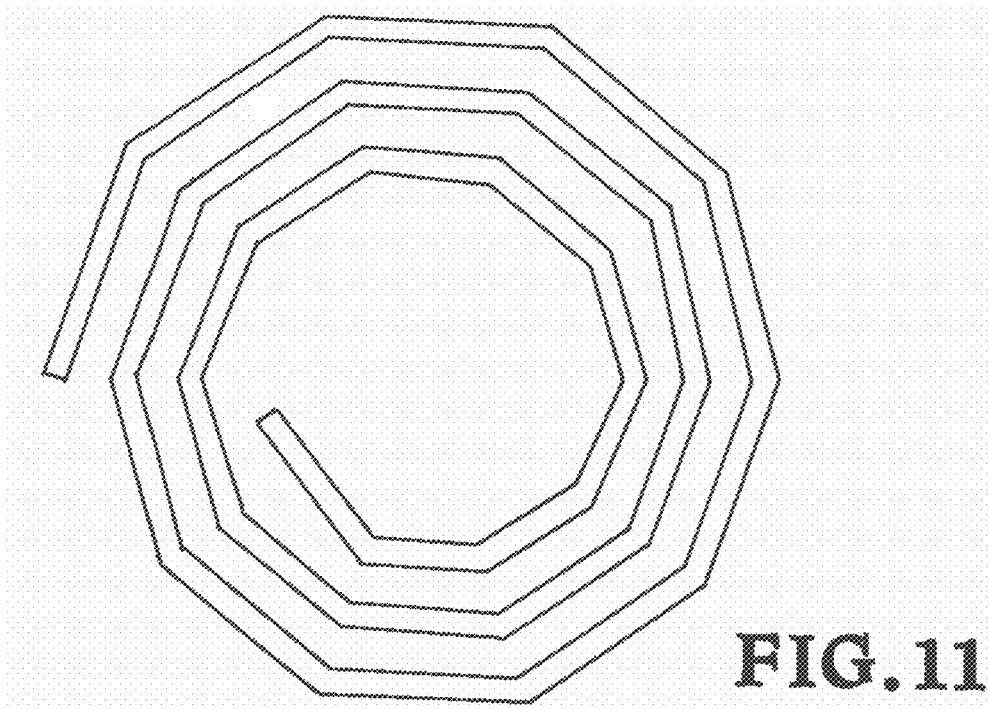
FIG. 11 is a top view of an example polygonal spiral embodiment of the cable section of the present invention.
Figure 12:
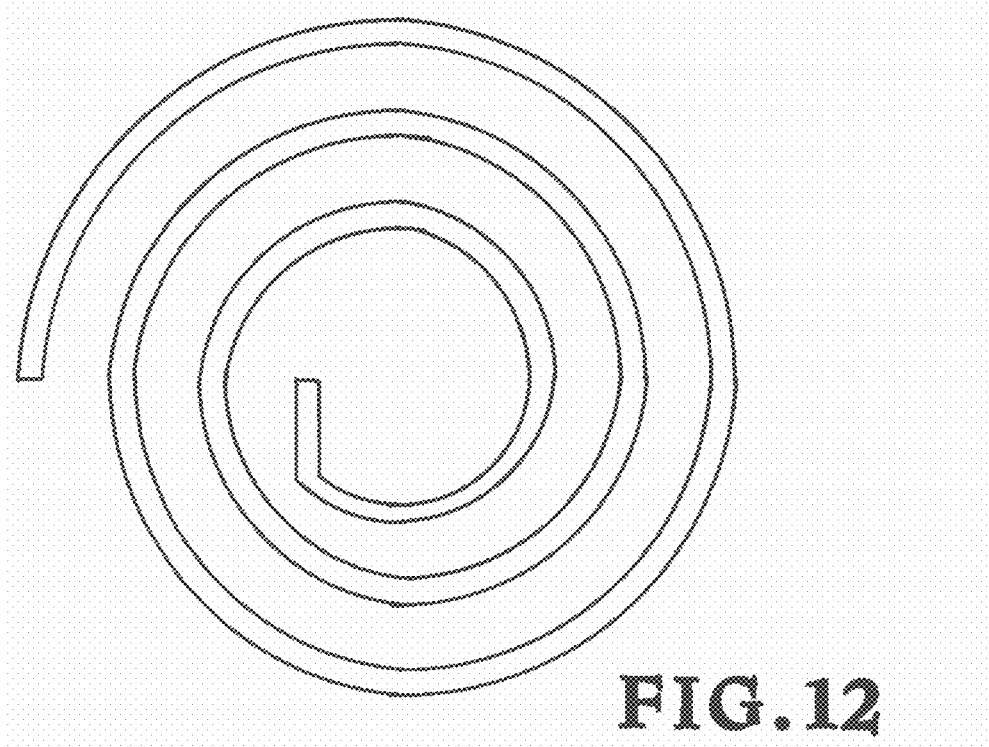
FIG. 12 is a top view of an example non-polygonal spiral embodiment of the cable section of the present invention.
Figure 13:
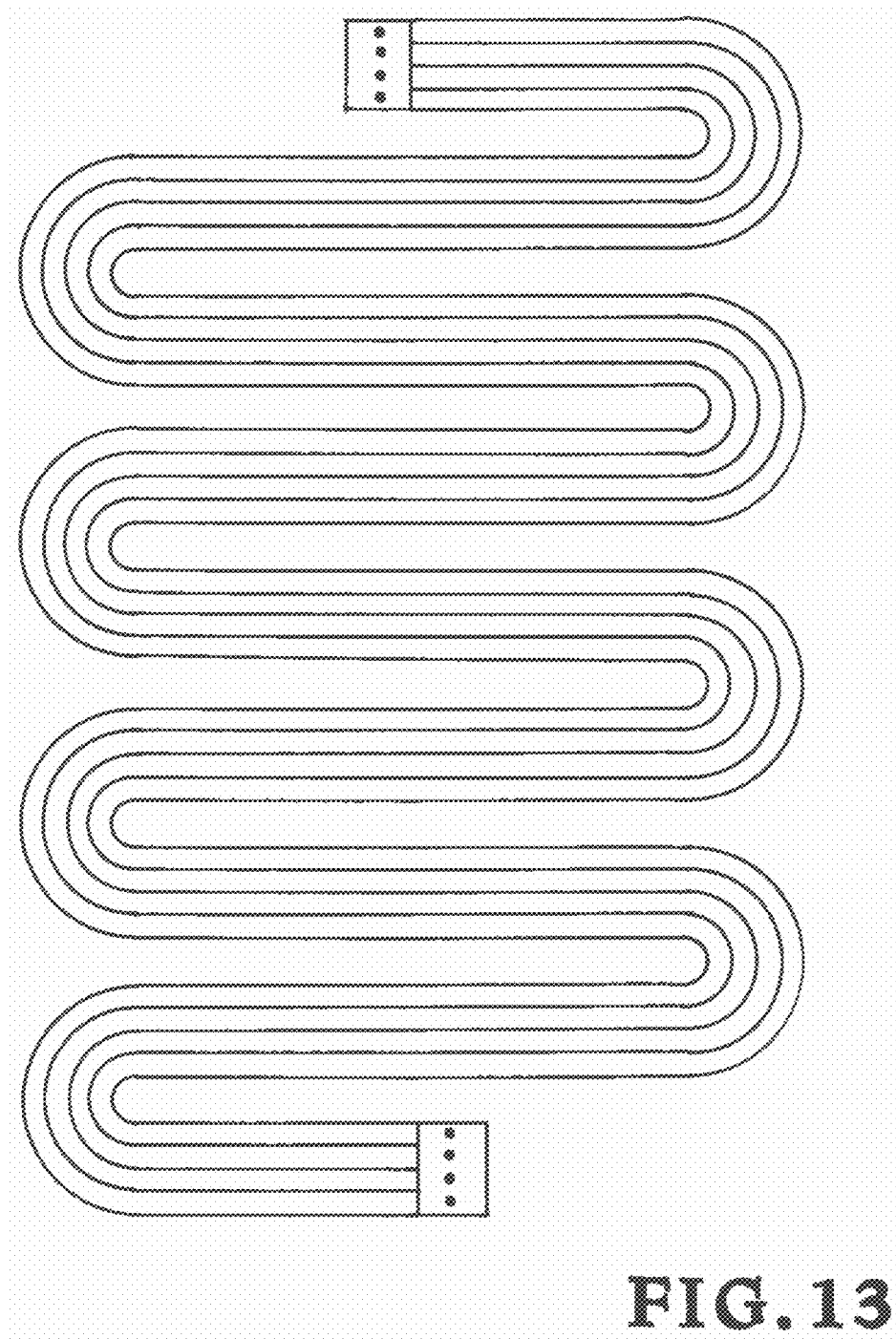
FIG. 13 is a top view of an example serpentine embodiment of the cable section of the present invention, showing switchbacks.

Ideally, the flat pattern of the planar structure that forms the cable section would be straight, but because the length of the cable may be larger than maximum dimension that can be defined in the fabrication process, the flat shape of the planar structure used to form the cable section is a polygonal spiral. The angle of the corners in the polygon is determined by the desired helix angle of the coil. FIGS. 11-13 show example planar layouts of a polygonal spiral (FIG. 11), non-polygonal spiral (FIG. 12), and a serpentine electrode array (FIG. 13). Because it is not a straight section, when the planar structure is wound into a helix of constant pitch, the flat section will fold. This fold occurs near the corners of the polygon.

Rather than using a polygonal spiral for the flat pattern used to form the cable, it may be possible to use a true spiral with a radius that varies linearly with angle. The disadvantage of using this structure is that coiling this structure into a constant pitch helix will require folds in the planar structure that are difficult to control.

In this embodiment, the cable section of the planar structure meets the rectangular electrode section at an angle. This angle is nominally equal to the helix angle of the cable.

To maintain flexibility of the final cable structure, it is desirable to keep the flat pattern of the cable section from overlapping itself when formed as a helix. As a result, the maximum width of the flat pattern of the cable section is dictated by the diameter and pitch of the helix. At the limit, the width must be less than the circumference of the cylinder that defines the helix.

The cylindrical core of the device is a flexible cylindrical rod that is made of a polymer, which may be a thermoplastic (such as polyurethane) or a thermoset (such as silicone). The core cylinder may have constant diameter along its length, or it may have sections of different diameters. In particular, the electrode section may have a different (typically larger) core diameter than the cable section. In one example embodiment, the core cylinder includes a hollow core that is concentric with the outer diameter and runs the entire length of the device but is closed at the very tip of the electrode section. The hollow core is intended to receive a stylet, which is temporarily inserted to aid in device insertion into the brain during surgery.

A relatively thin layer of polymer (not shown in figures) is also provided to cover the entire length of the cable section. This outer jacket serves to hold the cable helix in place and to form the outer surface of the cable section. The outer jacket also serves to prevent the cut edges of the planar structure from damaging the local tissue. The outer jacket may extend into the electrode section, but is at least patterned such that the metal electrodes remain exposed. The outer jacket may also be patterned to form a narrow strip to cover the seam where the long edges of the cylindrical planar structure forming the electrode region meet.

The electrode section may include a formed tip, which covers the end of the electrode cylinder.

In one example embodiment, the planar structure may be constructed in on a handle wafer using micro-fabrication techniques such as material deposition, photolithography, and etching. In other embodiments, the planar structure may be fabricated using bonded layers, laser cutting, etc. Whether or not the core cylinder is solid or a hollow tube, it may be formed by similar techniques such as extrusion, dipping, injection molding, or compression molding.

In an example embodiment, a first step in forming the planar structure into the final shape is to form the electrode section into a cylinder. This can be accomplished by a number of techniques, hut in one example embodiment a progressive folder is used. The planar structure is then pulled through the die, progressively forming the electrode region into a cylinder. The cylinder is held in place in a cylindrical form along its entire length. With the electrode cylinder still in the form, the core cylinder is inserted into the void at the center of the electrode region. In the case where the core cylinder is hollow, the insertion step is facilitated by first capping or sealing the end of the core cylinder, and then inserting a stylet into the hollow core.

Once the core is fully extended into the folded planar electrode region, heat is applied to the entire form assembly to promote adhesion between the core and the planar structure. After cooling, the form is removed leaving the temporarily formed electrode region. Both the stylet and the cylindrical form should be made of or coated with a material that does not bond easily with the core material.

Figure 9:
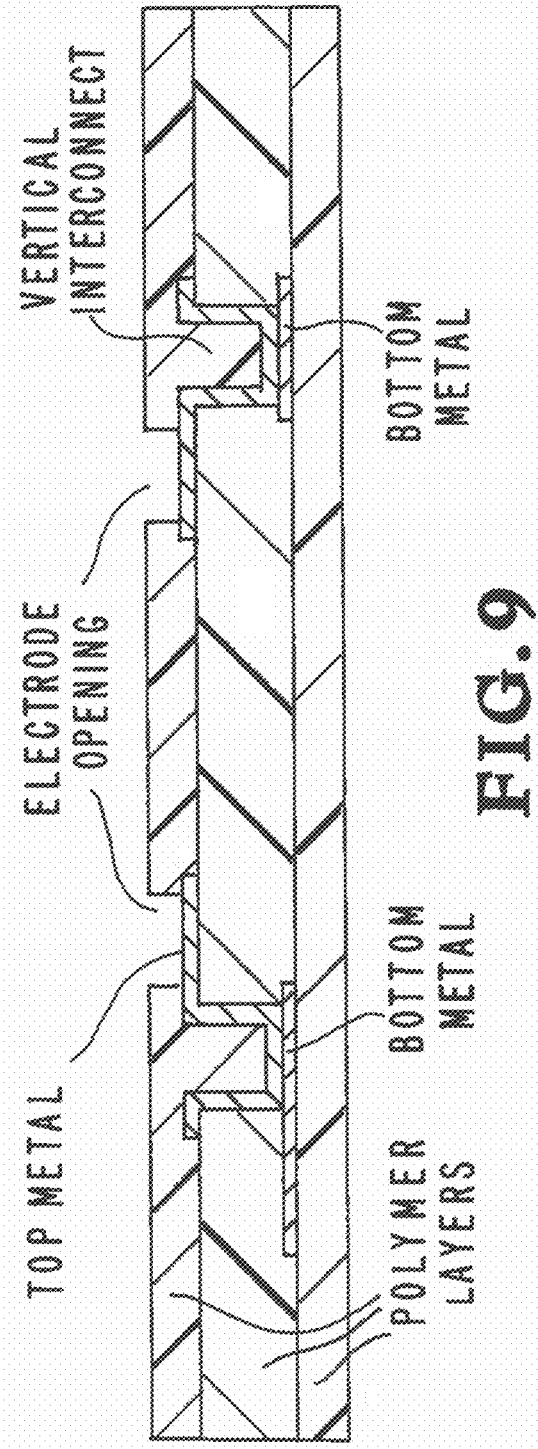
FIG. 9 is a cross-sectional view of an example embodiment of the cylindrical electrode array showing vertical interconnects separating the electrode layer from the trace layer, while maintaining electrical connection.

With the electrode region temporarily formed, the entire assembly, including the stylet, is placed into a coiling device. The coiling device has chucks on both ends that are used to hold the ends of the assembly. The coiling device allows for both chucks to be rotated at the same rate, which has the effect of rotating the entire assembly. Using this rotating motion, the cable section of the planar structure is wound around the cylindrical core at a constant pitch over its entire length. FIG. 9 shows a schematic of a coiled cable around a hollow polymer core.

Once the planar structure is coiled around the core tubing, it may be temporarily secured in place. In the case of thermoplastic core tubing, this can be accomplished by raising the surface temperature of the assembly such that the core tubing melts slightly and adheres to the planar structure. After cooling, the planar structure is held in its helical shape by the adhesion to the core tubing. This adhesion may also be accomplished with a pressure sensitive adhesive or a curing adhesive. In the case where the core tubing is silicone, a thin layer of silicone is used to adhere the planar structure to the core tubing.

After the electrode region and cable region are temporarily formed by adhesion to the core material, the outer jacket for the cable section is applied. The material for the outer jacket may be the same or a different material that was used for the core cylinder. The outer jacket material should be chosen primarily for its biocompatibility, mechanical, and insulating properties. The outer jacket may be formed by one of several methods, including dip coating, compression molding, injection molding, or by sliding an outer cylinder over the coiled assembly. In this embodiment, the outer jacket material is polyurethane, and the forming method is dip coating.

The next step is to apply the outer jacket in the electrode region and/or over the seam where the long edges of the planar structure that forms the electrode region meet. This process can be injection molding, compression molding, or via an additive process such as 3D printing. In this embodiment this process covers the seam only, and uses a compression molding technique.

The stylet, if used, can now be removed. The tip is then formed in a compression or injection molding step.

Figure 10A:
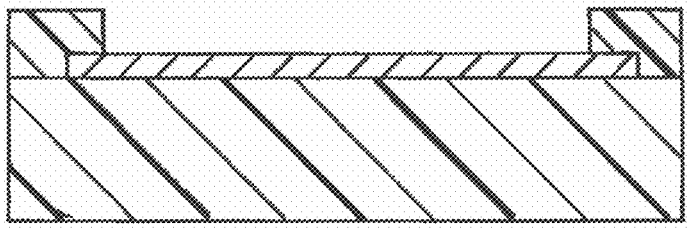
FIG. 10A shows a schematic side view of standard electrode in which a base polymer is deposited, an electrode metal is deposited and patterned, a top layer of polymer is deposited, and an opening in the polymer is opened to create the electrode site.
Figure 10B:
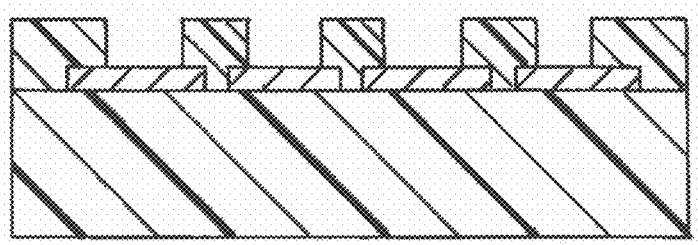
FIG. 10B shows a schematic side view of a segmented electrode, which may be used in the present invention, in which a series of small electrode pads form a single large electrode.
Figure 10C:
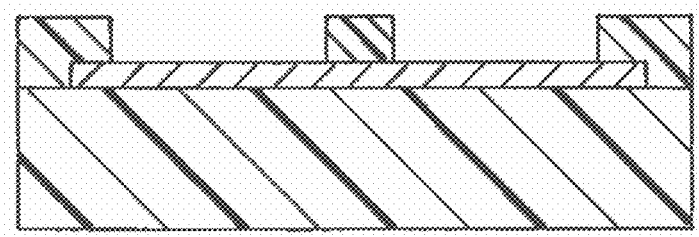
FIG. 10C shows a schematic side view of a segmented electrode, which may be used in the present invention, in which the metal electrode is continuous, but the insulating polymer is kept intact over many regions of the electrode, thereby acting as a mechanical member that balances stress of the electrode array.

FIGS. 14 and 15 together show a second example embodiment of the cylindrical electrode array of the present invention. In this embodiment, the cable section comprises a plurality of strand where each comprises a multilayer having at least one conductive trace, which the electrode and connector regions are similar to that described in the first example embodiment in FIGS. 1-5. As shown, the cable region is a multi-stranded cable. Each strand consists of a smaller subset of the total number of conductive traces. For example, in a 32-channel system, a single strand may be a sandwich structure of metal and polymer where as few as a single trace is encapsulated. The stranded traces region covers a portion of, or the entire cable region. FIG. 10 shows top view of an example electrode array with a multi-stranded cable region. And FIG. 11 shows a cross-section example of a stranded cable region showing distinct strands consisting of traces encapsulated in polymer in order to achieve long cable lengths, the stranded region may be straight, spiral, circular, polygonal with shallow angle bends (less than 90 degrees), or a serpentine shape. The planar device shape may be corrected in order to achieve consistent strand length in a coiled or circular design.

In an example method of constructing the device of FIGS. 14 and 15, the electrode region is folded into a cylinder as described above, and a hollow polymer core is inserted into the inner diameter of the electrode region using a stylet. Next, the stranded cable is twisted around the core in a helical coil, wherein the location of the individual strands may or may not be controlled with the coiling device. Once coiled, similar to the above description, the strands are adhered to the polymer core by using a heating step. After this step, an outer polymer jacket is formed around the multi-stranded cable. This can be done by a method such as dip-coating, or by sliding an outer jacket over the coiled region followed by a polymer reflow at elevated temperature.

Although the description above contains many details and specifics, these should not be construed as limiting the scope of the invention but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present invention fully encompasses other embodiments which may become obvious to those skilled in the art. In the claims, reference to an element in the singular is not intended to mean "one and only one" unless explicitly so stated, but rather "one or more," All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims No claim element herein is to be construed under the provisions of 35 U.S.C. 112, sixth paragraph, unless the element is expressly recited using the phrase "means for."

We claim:

1. A cylindrical microelectrode array, comprising:
   an elongated cylindrical core; and
   a multilayer structure conformally folded around and affixed to the cylindrical core so as to extend between opposite ends thereof, said multilayer structure having integrated sections comprising:
   a multilayer electrode section having a plurality of electrodes exposed through electrically insulating layers, and conformally folded around and affixed to a first one of the opposite ends of said elongated cylindrical core,
   a multilayer connector section having a plurality of conductive bond pads exposed through electrically insulating layers for interfacing with external electronics, and conformally folded around and affixed to a second one of the opposite ends of said elongated cylindrical core, and
   a multilayer cable section connecting between the multilayer electrode and connector sections and conformally folded around and affixed to the elongated cylindrical core between the opposite ends thereof, and having a plurality of conductive traces encapsulated in electrically insulating layers and which connect between the electrodes and their corresponding bond pads.

2. The cylindrical microelectrode array of claim 1, wherein the multilayer electrode section of the multilayer structure has a substantially rectangular planar layout so that opposite longitudinal edges of the multilayer electrode section connect to form a seam when conformally folded around and affixed to the cylindrical core.

3. The cylindrical microelectrode array of claim 1, wherein the multilayer cable section of the multilayer structure is helically coiled around the cylindrical core.

4. The cylindrical microelectrode array of claim 1, wherein both the multilayer electrode and cable sections of the multilayer structure are helically coiled around the cylindrical core.

5. The cylindrical microelectrode array of claim 1, wherein the multilayer cable section of the multilayer structure has a planar layout that is selected from the group consisting of polygonal spiral, non-polygonal spiral, and serpentine with switchbacks.

6. The cylindrical microelectrode array of claim 1, wherein the multilayer cable section includes a plurality of multilayer strands extending between the multilayer electrode and connector regions, with each strand having at least one insulated conductive trace.

7. The cylindrical microelectrode array of claim 1, wherein the elongated cylindrical core is hollow to receive a stylet therein.

8. A method of fabricating a cylindrical microelectrode array, comprising:
   providing a planar multilayer structure having a multilayer electrode section with a plurality of electrodes exposed through electrically insulating layers, and multilayer connector section having conductive bond pads for interfacing with external electronics; and a multilayer cable section having insulated electrical conduits connecting between the bond pads of the multilayer connector section with the electrodes of the multilayer electrode section; and
   conformally folding the planar multilayer structure around and affixing to a cylindrical core so that the multilayer electrode section is conformally folded around and affixed to a first one of the opposite ends of said elongated cylindrical core, the multilayer connector section is conformally folded around and affixed to a second one of the opposite ends of said elongated cylindrical core, and the multilayer cable section is conformally folded around and affixed to the elongated cylindrical core between the opposite ends thereof, and the plurality of electrodes are distributed radially and/or axially along a cylindrical axis of the cylinder core.

9. The method of claim 8,
wherein the step of conformally folding the planar multilayer structure around and affixing to the cylindrical core includes helically coiling the multilayer cable section around the cylindrical core.

\* \* \* \* \*